United States Patent [19]

Davidson et al.

[11] Patent Number: 5,057,510
[45] Date of Patent: Oct. 15, 1991

[54] USE OF SELECTED PYRIDINE-2-THIONE-N-OXIDE COMPOUNDS AS GROWTH PROMOTERS FOR POULTRY

[75] Inventors: Jeffrey N. Davidson, Tulare, Calif.;
John H. Wedig, Guilford, Conn.;
John G. Babish, Ithaca, N.Y.;
Richard A. McMillan, Exeter, Calif.

[73] Assignee: Olin Corporation, Cheshire, Conn.

[21] Appl. No.: 677,630

[22] Filed: Dec. 3, 1984

Related U.S. Application Data

[63] Continuation-in-part of Ser. No. 532,883, Sep. 16, 1983, abandoned.

[51] Int. Cl.$^5$ ............................................. A61K 31/555
[52] U.S. Cl. .................................................... 514/188
[58] Field of Search ............................................ 514/188

[56] References Cited

U.S. PATENT DOCUMENTS

| | | | |
|---|---|---|---|
| 3,778,508 | 12/1973 | Marco et al. | 424/300 |
| 4,282,228 | 8/1981 | De Getter et al. | 424/251 |
| 4,315,025 | 2/1982 | Danley | 424/274 |
| 4,399,130 | 8/1983 | Davidson et al. | 424/245 |
| 4,401,666 | 8/1983 | Wedig et al. | 424/245 |
| 4,454,137 | 6/1984 | Menon et al. | 424/245 |
| 4,463,009 | 7/1984 | Sanders | 424/263 |
| 4,505,917 | 3/1985 | Menon et al. | 514/347 |

FOREIGN PATENT DOCUMENTS 83305392.9 9/1983 European Pat. Off. .

*Primary Examiner*—Frederick E. Waddell
*Assistant Examiner*—K. Weddington
*Attorney, Agent, or Firm*—William A. Simons

[57] ABSTRACT

A method for improving the growth response in poultry comprising administering to said poultry a growth-promoting amount of at least one pyridine-2-thione-N-oxide compound selected from the group consisting of
(a) a metallic salt of pyridine-2-thione-N-oxide;
(b) 2,2'-dithiobispyridine-1,1'-dioxide; and
(c) adducts of 2,2'-dithiobispyridine-1,1'-dioxide, the adducts having the formula $(C_5H_4NOS)_2MY_t$ wherein M is an alkaline earth metal selected from the group consisting of calcium, magnesium, barium and strontium, Y is an anion selected from the group consisting of halides, sulfates, nitrates, chlorates and acetates, and t is either 1 or 2.

14 Claims, No Drawings

USE OF SELECTED PYRIDINE-2-THIONE-N-OXIDE COMPOUNDS AS GROWTH PROMOTERS FOR POULTRY

RELATED U.S. PATENT APPLICATION

This is a continuation-in-part patent application Ser. No. 532,883 filed by the same inventors on Sept. 16, 1983, now abandoned.

BACKGROUND OF THE INVENTION

1. Field of the Invention

This invention relates to the use of selected pyridine-2-thione-N-oxide compounds as growth promoters in poultry.

2. Description of the Prior Art

It has been found in recent years that poultry will gain more weight and gain it faster when various classes of compounds such as vitamins, minerals, estrogens, antibiotics, and tranquilizers are added to the diet. Although the presently available compounds are useful, new materials are still being sought that would produce weight gains more rapidly, to a greater extent, and more efficiently with respect to feed intake at a lower cost and without undesirable side effects.

BRIEF SUMMARY OF THE INVENTION

Accordingly, the present invention is directed to a method for improving the growth response in poultry such as turkeys and chickens which comprises administering (e.g. in feed) to the poultry a growth-promoting amount of at least one pyridine-2-thione-N-oxide compound selected from the group consisting of:

(a) a metallic salt of pyridine-2-thione-N-oxide;
(b) 2,2'-dithiobispyridine-1,1'-dioxide; and
(c) adducts of 2,2'-dithiobispyridine-1,1'-dioxide, the adducts having the formula

$(C_5H_4NOS)_2MY_t$ wherein M is an alkaline earth metal selected from the group consisting of calcium, magnesium, barium and strontium, Y is an anion selected from the group consisting of halides, sulfates, nitrates, chlorates and acetates, and t is either 1 or 2.

The present invention is also directed to feed compositions which contain a growth-promoting amount of at least one said pyridine-2-thione-N-oxide compound.

DETAILED DESCRIPTION

As stated above, metallic salts of pyridine-2-thione-N-oxide are a well-known class of compounds and are generally made by reacting a metallic salt with 2-mercaptopyridine-N-oxide. Suitable metallic salts of pyridine-2-thione-N-oxide may be alkali metal salts such as sodium ($Na^{+1}$) and heavy metal salts such as zinc ($Zn^{+2}$), ferric ($Fe^{+3}$), cupric ($Cu^{+2}$) and other metal salts such as aluminum. Because of their commercial availability, the sodium and zinc salts of pyridine-2-thione-N-oxide are the most preferred metal salts.

The sodium salt of pyridine-2-thione-N-oxide, also known as 2-pyridinethiol-1-oxide, Na salt, is generally made by reacting a 2-halopyridine-N-oxide (e.g. 2-chloropyridine-N-oxide) with sodium hydrosulfide (NaSH) in aqueous solution under a slightly alkaline condition or with a mixture of sodium sulfide ($Na_2S$) and sodium hydrosulfide. Exemplary methods for making this compound are disclosed in U.S. Pat. No. 2,686,786, which issued to Shaw et al on Aug. 17, 1954; U.S. Pat. No. 3,159,640, which issued to McClure et al on Dec. 1, 1964; and U.S. Pat. No. 3,892,760, which issued to Hooks et al on July 1, 1975.

The zinc salt of pyridine-2-thione-N-oxide, also known as bis[1-hydroxy-2(1H) pyridinethionato] zinc, may be made by reacting a zinc salt (e.g., $ZnCl_2$ or $ZnSO_4$) with 2-mercaptopyridine-N-oxide as its sodium salt. Exemplary methods for making this compound are disclosed in U.S. Pat. No. 2,809,971, which issued to Bernstein et al on Oct. 15, 1957, and U.S. Pat. No. 4,080,329, which issued to Mantwyler on Mar. 21, 1978.

Other metallic salts of pyridine-2-thione-N-oxide are disclosed in U.S. Pat. No. 3,347,863, which issued to Ottman et al on Oct. 17, 1967, (aluminum); U.S. Pat. No. 3,953,450, which issued to Bouillon et al on Apr. 27, 1976, (aluminum); U.S. Pat. No. 2,809,971, which issued to Bernstein et al on Oct. 15, 1957, (manganese, nickel, ferric, ferrous, cupric, zinc, and many other heavy metal salts); and U.S. Pat. No. 4,209,506, which issued to Bouillon et al on June 24, 1980, (aluminum). All of above-noted U.S. Pat. Nos. are incorporated herein by reference in their entireties.

The above-noted pyridine-N-oxide disulfide compounds are well known chemicals which may be made by oxidation of the sodium salt of pyridine-2-thione-N-oxide, preferably with hydrogen peroxide or another oxidizing agent. U.S. Pat. No. 2,742,476, which issued to Bernstein et al on Apr. 17, 1956, discloses 2,2'-dithiobispyridine-1,1'-dioxide and its preparation. The adducts of 2,2'-dithiobispyridine-1,1'-dioxide listed in (c) above and their preparation are described in U.S. Pat. Nos. 3,818,018 and 3,890,434, which issued to Weisse et al on June 18, 1984 and June 17, 1975, respectively. All of these U.S. Pat. Nos. are incorporated herein by reference in their entireties.

Also included in the adducts are hydrates of the aforementioned compounds of formula (I), i.e. adducts including $nH_2O$ groups where n is an integer of 0 to 10.

The preferred disulfide compounds for use in this invention are 2,2'-dithiobispyridine-1,1'-dioxide and the magnesium sulfate trihydrate adduct of 2,2'-dithiobispyridine-1,1'-dioxide (i.e. M is magnesium, Y is sulfate and t is 1 with $3H_2O$ attached thereto).

In practicing the process of the present invention, poultry such as turkeys and chickens are administered with a growth-promoting amount of at least one of the above-noted pyridine-2-thione-N-oxide compound. It is to be understood that the term "growth-promoting" amount as used in the specification and claims herein is intended to include any amount or concentration of the above-noted active compounds that will cause an increase in the rate of weight gain in such animals or increase the feed efficiency in such animals. Of course, this amount may be changed in response to numerous variables, such as the degree of effectiveness required, the species of poultry, its age, its weight and the type of carrier employed, if any.

For most uses, it is preferred to administer the active compound or compounds in a feed composition which contains from about 3 to about 75 parts of active compound(s) per million parts by weight of total feed. These amounts of active compound(s) in feed will supply the poultry with a daily intake of from about 0.3 mg to about 7.5 mg of active compound(s) per kilogram of body weight per day. Administration of the active compounds(s) may commence for the birds shortly after hatching. Feeding may continue throughout the growing period. In addition to feeding the active compound(s) in combination with the feed, the active compound(s) may be orally administered in the form of tablets, capsules, powders, solutions, suspensions alone or in a liquid carrier such as the animals drinking water or with a pharmaceutical carrier by injection or implantation. Furthermore, the active compound or compounds used in the present process may be combined with other known veterinary and pharmaceutical agents for further benefits.

Advantageously, the active compound or compounds may be mixed into a poultry feed composition by means of a premix. This premix may be in the form of a liquid or solid wherein the concentration of the active compound(s) is about 100 to about 2000 times greater than the desired final concentration in the feed. For example, the active compound(s) may be dissolved or suspended in a fluid vehicle such as corn oil, cottonseed oil, molasses, distillers solubles and the like to prepare a fluid premix. Alternatively, a solid premix may be prepared by mixing the active compound(s) with an edible solid diluent such as sucrose, lactose, starch, corn meal, flour, calcium carbonate, soybean meal and the like.

The poultry feed composition useful with the present growth-promoting compounds may include any and all conventional poultry feed composition(s). They may include grains and fibrous materials such as dehydrated alfalfa, ground corn, oats, ground milo, soybean meal, cottonseed meal, silage, barley and the like. The poultry feeds may also contain natural oils, antioxidants, minerals such as bone meal, salt and the various trace minerals including salts of zinc, copper, manganese, magnesium, cobalt, iodine and iron. Antibiotics and other medicaments may be used. Various vitamins, particularly A, B, E and D complexes, may be added to provide for the deficiencies in these vitamins incident to the selection of the various components of the complete feed. Other basic nutrients may be used if desired or if they are necessary to satisfy the requirements of the complete ration.

It should be clearly understood that any of the above-noted ingredients which may make up such feed formulations, other than the active compound or compounds, may include any and all known and conventional substances in amounts that are suitable and do not hinder the desired growth promotion result. Therefore, such process parameters are not critical to the present invention.

Besides the above-noted active compounds, the present invention also contemplates the use of similar pyridine-2-thione-N-oxide compounds. Specifically, the present invention contemplates the use of free 2-mercaptopyridine-N-oxide, organic salts (e.g., t-butylamine) and adducts of 2-mercaptopyridine-N-oxide. The present invention also contemplates the use of similar compounds which have one or more other substituents on the pyridine ring (e.g., lower alkyl groups, $NO_2$, or halogens).

Besides poultry, the present invention contemplates the administration of growth-promoting amounts of one or more of the present active compounds to other meat-producing farm animals such as ruminating animals such as beef cattle and sheep.

The following Example further illustrates the present invention. All parts and percentages are by weight unless explicitly stated otherwise.

EXAMPLE 1

A turkey feed (called "Pre-Starter") for very young turkeys (0–3 weeks of age) was prepared from the following amounts and types of ingredients:

| INGREDIENTS | POUNDS |
| --- | --- |
| Alfalfa | 62. |
| Corn | 425. |
| Dried Brewers Yeast | 50. |
| Soy Meal | 425. |
| Ground Tankage | 37. |
| Whey | 12. |
| Calcium Diphosphate | 28. |
| Limestone | 6. |
| Vegetable Oil | 6. |
| Starter Vitamins[1] | 2.25 |
| Salt | 2.25 |
| Sulfur Supplement[2] | 1.25 |
| Methionine | 1.25 |
| Trace Minerals[3] | 0.375 |
| Total | 1,058.375 |

[1]Choline, thiamine HCl, riboflavin, niacin, pyridoxine · HCl, folacin, biotin, and vitamins A, $B_6$, $B_{12}$, $D_3$, E and K
[2]Dyanamate produced by International Minerals and Chemical Corporation of Des Plaines, IL
[3]Potassium, sodium, chlorine, copper, iodine, iron, magnesium, manganese, selenium and zinc A turkey feed (called "Starter No. 1" diet) for young turkeys (4–6 weeks of age) was prepared from the following types and amounts of ingredients:

| INGREDIENTS | POUNDS |
| --- | --- |
| Alfalfa | 1.25 |
| Grape | 50. |
| Corn | 400. |
| Dried Brewers Yeast | 50. |
| Soy Meal | 400. |
| Ground Tankage | 37.5 |
| Whey | 12.5 |
| Calcium Diphosphate | 22.5 |
| Limestone | 6.25 |
| Vegetable Oil | 6.25 |
| Starter Vitamins[1] | 2.5 |
| Sulfur Supplement[2] | 1.25 |
| Methionine | 1. |
| Trace Minerals[3] | 0.375 |
| Total | 1,021.375 |

This Starter No. 1 diet was mixed with three buckets of grits[4] before being fed to turkeys.
[1]Choline, thiamine HCl, riboflavin, niacin, pyridoxine · HCl, folacin, biotin, and vitamins A, $B_6$, $B_{12}$, $D_3$, E and K
[2]Dyanamate produced by International Minerals and Chemical Corporation of Des Plaines, IL
[3]Potassium, sodium, chlorine, copper, iodine, iron, magnesium, manganese, selenium and zinc
[4]Added organics to help digestion. No nutritional value A turkey feed (called "Starter No. 2" diet) for young turkeys (7–9 weeks of age) was prepared from the following types and amounts of ingredients:

| INGREDIENTS | POUNDS |
| --- | --- |
| Alfalfa | 62.5 |
| Corn | 700. |
| Rice | 200. |
| Grape | 150. |
| Dried Brewers Yeast | 100. |
| Soy Meal | 700. |
| Meal Meal | 75. |
| Calcium Diphosphate | 30. |
| Limestone | 10. |
| Starter Vitamins[1] | 5. |
| Sulfur Supplement[2] | 2.5 |
| Methionine | 2. |

| INGREDIENTS | POUNDS |
|---|---|
| Trace Minerals[3] | 0.75 |
| Total | 2,037.75 |

This Starter No. 2 diet was mixed with 1.5 buckets of grits[4] before being fed to turkeys.
[1]Choline, thiamine HCl, riboflavin, niacin, pyridoxine · HCl, folacin, biotin, and vitamins A, $B_6$, $B_{12}$, $D_3$, E and K
[2]Dynamate produced by International Minerals and Chemical Corporation of Des Plaines, IL
[3]Potassium, sodium, chlorine, copper, iodine, iron, magnesium, manganese, selenium and zinc
[4]Added inorganics to help digestion. No nutritional value Three groups of 600 turkeys (from 0–9 weeks) were each fed the above-noted feed formulations to determine if zinc pyridine-2-thione-N-oxide was an effective growth promoter. One group received 25 parts per million of zinc pyridine-2-thione-N-oxide in their feed. The second group received 10 parts per million of zinc pyridine-2-thione-N-oxide in their feed. The third group was a control group with no zinc pyridine-2-thione-N-oxide added to their feed.

The zinc pyridine-2-thione-N-oxide was added to the feed by means of a premix. This premix consisted of the active compound as well as powdered milk and corn meal and was formulated so that 2 or 5 pounds of premix added to one ton of feed would yield a finished medicated diet at 10 parts or 25 parts per million, respectively, of active compound. Specifically, this premixing was accomplished by adding 133.32 grams of zinc pyridine-2-thione-N-oxide to 454 grams of powdered milk to give a total of 587.32 grams of medicated milk concentrate (0.227 grams of active compound per gram of concentrate). Then 20.0 grams of this concentrate was mixed with 434 grams of corn meal to give 454 grams (1 pound) of finished premix. Each pound of this premix contains 0.01 pound of zinc pyridine-2-thione-N-oxide. Therefore, 2 pounds of premix added to 2,000 pounds of feed would equal about 10 parts of zinc pyridine-2-thione-N-oxide per million parts of feed. Five pounds of premix to 2,000 pounds of feed would equal about 25 parts of zinc pyridine-2-thione-N-oxide per million parts of feed.

The three groups of turkeys consisted of 300 No. 33's (snood) and 300 of No. 45 (desnood). All of the turkeys received a 10 mg injection of streptomycin plus vitamins at the hatchery. No other medication was given to the birds.

The results of this testing are given in Table I below. Group I is the group given 25 ppm of zinc pyridine-2-thione-N-oxide. Group II is the group given 10 ppm of zinc pyridine-2-thione-N-oxide. Group III is the control group given no zinc pyridine-2-thione-N-oxide.

TABLE I

| Group Identification | Ending Birds | Average Weight (Pounds) | Total Bird Weight (Pounds) | Total Feed | Feed Efficiency | Mortality (%) |
|---|---|---|---|---|---|---|
| I-33 | 270 | 4.409 | 1190.43 | 5910.25 | 2.5483 | 11.5 |
| I-45 | 261 | 4.352 | 1128.82 | | | |
| II-33 | 228 | 3.594 | 819.43 | 4505.25 | 2.6472 | 23.5 |
| II-45 | 222 | 3.975 | 882.45 | | | |
| III-33 | 231 | 3.825 | 883.57 | 4985.25 | 2.6754 | 17.6 |
| III-45 | 234 | 4.187 | 979.76 | | | |

The food efficiency was determined as the ratio of pounds of feed consumed per pound of body weight. At the dose of 10 parts of zinc pyridine-2-thione-N-oxide per million parts of feed (Group II) no statistical difference was noted with respect to weight of the bird, or a difference in food efficiency as compared to the control group. At a level of 25 parts of zinc pyridine-2-thione-N-oxide per million parts of feed (Group I) a statistical difference was noted when this group was compared to the controls. Specifically, a 10% difference in weight gain over the control was noted; and an 8.0% gain in food efficiency was noted in the treated birds vs. the controls. It should be noted that not all of the 600 birds in each group lived through the whole test period; however, the level of mortality was less in Group I than with the other two groups.

EXAMPLE 2

A turkey feed (called "Starter" diet) for young turkeys (0–8 weeks of age) was prepared from the following types and amounts of ingredients:

| INGREDIENTS | POUNDS |
|---|---|
| Alfalfa | 1.25 |
| Grape | 50. |
| Corn | 400. |
| Dried Brewers Yeast | 50. |
| Soy Meal | 400. |
| Ground Tankage | 37.5 |
| Whey | 12.5 |
| Calcium Diphosphate | 22.5 |
| Limestone | 6.25 |
| Vegetable Oil | 6.25 |
| Starter Vitamins[1] | 2.5 |
| Sulfur Supplement[2] | 1.25 |
| Methionine | 1. |
| Trace Minerals[3] | 0.375 |
| Total | 1,021.375 |

This Starter No. 1 diet was mixed with three buckets of grits[4] before being fed to turkeys.
[1]Choline, thiamine HCl, riboflavin, niacin, pyridoxine · HCl, folacin, biotin, and vitamins A, $B_6$, $B_{12}$, $D_3$, E and K
[2]Dyanamate produced by International Minerals and Chemical Corporation of Des Plaines, IL
[3]Potassium, sodium, chlorine, copper, iodine, iron, magnesium, manganese, selenium and zinc
[4]Added organics to help digestion. No nutritional value Five groups of 60 turkeys (from 0–56 days) were each fed for 56 days the above-mentioned feed formulation to determine if zinc pyridine-2-thione-N-oxide (also referred to as ZPT in this Example) was an effective growth promoter. The groups received the following parts per million in their feed respectively, 0, 3, 10, 30 and 100. The 0 parts per million group was the control.

The zinc pyridine-2-thione-N-oxide was added to the feed by means of a premix. This premix consisted of the active compound as well as turkey feed and was formulated so that 1 kilogram of premix added to 453 kilograms of feed would yield a finished medicated diet at 3, 10, 30 or 100 parts per million. The pyridine-2-thione-N-oxide was microencapsulated in a fatty acid (linoleic acid) to prevent degradation in the feed. The encapsulated product was 21% active material by weight. Specifically, this premix was made by adding the following quantities of zinc pyrithione-2-thione-N-oxide to 1 kilogram of turkey feed—0, 6.4, 21.2, 64 and 213 grams. Each of these were then added to 453 kilograms of feed to attain the desired medicated diet. Analysis of the feed for the ZPT content confirmed their concentration.

Each of the five groups of turkeys used were of split sexes, 10 males and 10 females per each of the three subgroups for each group. All of the turkeys received a 10 mg injection of streptomycin plus vitamins at the hatchery. No other medication was given to the birds. The birds were randomly assigned to brooding batteries for the test after their sex was determined.

The results of this testing are given in Tables II and III below.

TABLE II

Effect of Dietary ZPT on Turkey Body Weight
Dietary ZPT Concentrations

| WEEK | 0 ppm | 3 ppm | 10 ppm | 30 ppm | 100 ppm |
|---|---|---|---|---|---|
| 0 | 51 ± .3 g. | 51 ± .3 g. | 51 ± .3 g. | 51 ± .4 g. | 51 ± .3 g. |
| 1 | 102 ± 1 | 102 ± 1 | 101 ± 1 | 98 ± 1 | 87 ± 2* |
| 2 | 230 ± 4 | 215 ± 3* | 210 ± 4* | 205 ± 4* | 173 ± 3* |
| 3 | 448 ± 7 | 438 ± 6 | 436 ± 7 | 414 ± 7* | 347 ± 6* |
| 4 | 654 ± 18 | 668 ± 17 | 663 ± 15 | 645 ± 15 | 591 ± 10* |
| 5 | 994 ± 23 | 1025 ± 25 | 974 ± 25 | 993 ± 20 | 890 ± 17* |
| 6 | 1407 ± 35 | 1482 ± 39* | 1443 ± 37 | 1398 ± 42 | 1343 ± 24* |
| 7 | 1972 ± 41 | 2034 ± 55* | 1992 ± 49 | 1977 ± 46 | 1859 ± 35* |
| 8 | 2368 ± 49 | 2530 ± 67* | 2515 ± 60* | 2407 ± 56 | 2354 ± 45* |

The above body weights indicated with a * are significantly different from the control group ($p < 0.05$). All of these body weights are mean values ± the standard error of the mean.

TABLE III

Overall Feed Efficiency with ZPT

| Treatment | Feed Efficiency |
|---|---|
| 0 ppm | 1.920 |
| 3 ppm | 1.812* |
| 10 ppm | 1.826* |
| 30 ppm | 1.863 |
| 100 ppm | 1.912 |

Averaged over the 8 week period.
Feed Efficiency is defined as gms of feed consumed per gms increase in body weight. The feed efficiency values indicated with an * are significantly different than the control ($p < 0.05$).

A statistically significant increase ($p < 0.05$) was noted in the body weight of the 3 ppm (6.8%) and 10 ppm (6.2%) ZPT treated groups vs. the controls after 8 weeks. The dose of 100 ppm caused a significant decrease ($p < 0.05$) in body weight since the dose was too high thereby causing the toxicity (i.e. paresis of wings and legs and ataxia).

As stated above, the body efficiency was determined as the ratio of pounds of feed consumed per pound of body weight. At a level of 3 and 10 ppm, there was a statistical difference ($p < 0.05$) of 5.9% and 5.1% respectively vs. the controls—the birds treated with 3 and 10 ppm ZPT ate less and gained more weight than the controls.

EXAMPLE 3

A turkey feed (called "Starter" diet) for young turkeys (0-8 weeks of age) was prepared from the following types and amounts of ingredients:

| INGREDIENTS | POUNDS |
|---|---|
| Alfalfa | 1.25 |
| Grape | 50. |
| Corn | 400. |
| Dried Brewers Yeast | 50. |
| Soy Meal | 400. |
| Ground Tankage | 37.5 |
| Whey | 12.5 |

-continued

| INGREDIENTS | POUNDS |
|---|---|
| Calcium Diphosphate | 22.5 |
| Limestone | 6.25 |
| Vegetable Oil | 6.25 |
| Starter Vitamins[1] | 2.5 |
| Sulfur Supplement[2] | 1.25 |
| Methionine | 1. |
| Trace Minerals[3] | 0.375 |
| Total | 1,021.375 |

This Starter No. 1 diet was mixed with three buckets of grits[4] before being fed to turkeys.
[1]Choline, thiamine HCl, riboflavin, niacin, pyridoxine · HCl, folacin, biotin, and vitamins A, $B_6$, $B_{12}$, $D_3$, E and K
[2]Dyanamate produced by International Minerals and Chemical Corporation of Des Plaines, IL
[3]Potassium, sodium, chlorine, copper, iodine, iron, magnesium, manganese, selenium and zinc
[4]Added organics to help digestion. No nutritional value Five groups of 60 turkeys were each fed for 56 days the above-mentioned feed formulations to determine if magnesium sulfate trihydrate adduct of 2,2'-dithiobispyridine-1,1'-dioxide was an effective growth promoter. The groups received the following parts per million in their feed respectively, 0, 3, 10, 30 and 100. The 0 parts per million group was the control.

The magnesium sulfate trihydrate adduct of 2,2'-dithiobispyridine-1,1'-dioxide was added to the feed by means of a premix. This premix consisted of the active compound as well as turkey feed and was formulated so that 1 kilogram of premix added to 545 kilograms of feed would yield a finished medicated diet at 3, 10, 30 or 100 parts per million. The magnesium sulfate trihydrate adduct of 2,2'-dithiobispyridine-1,1'-dioxide was microencapsulated in a fatty acid (linoleic acid) to prevent degradation of the feed. The encapsulated product was 20% active material by weight. Specifically, this premix was accomplished by adding the following quantities of magnesium sulfate trihydrate adduct of 2,2 -dithiobispyridine-1,1'-dioxide to 1 kilogram of turkey feed—8.5, 28.3, 85, and 231.9 grams. Each of these were then added to 545 kilograms of feed to attain the desired medicated diet.

Each of the five groups of turkeys used were of split sexes, 10 males and 10 females per each of the three subgroups for each group. All of the turkeys received a 10 mg injection of streptomycin plus vitamins at the hatchery. No other medication was given to the birds. The birds were randomly assigned to brooding batteries for the test after their sex was determined.

The results of this testing are given in Table IV below.

TABLE IV

Effect of Dietary Magnesium Sulfate Trihydrate Adduct of 2,2'-dithiobispyridine-1,1'-dioxide on Turkey Body Weight*
Dietary Magnesium Sulfate Trihydrate Adduct of 2,2'-dithiobispyridine-1,1'-dioxide Concentrations

| WEEK | 0 ppm | 3 ppm | 10 ppm | 30 ppm | 100 ppm |
|---|---|---|---|---|---|
| 1 | 49 | 50 | 49 | 49 | 50 |
| 2 | 119 | 116 | 112 | 119 | 112 |
| 3 | 222 | 226 | 209 | 223 | 192* |
| 4 | 446 | 465 | 429 | 453 | 385* |
| 5 | 707 | 725 | 671 | 716 | 615* |
| 6 | 1135 | 1181 | 1116 | 1151 | 1020* |
| 7 | 2196 | 2301* | 2217 | 2282 | 2007* |
| 8 | 2643 | 2776* | 2678 | 2755* | 2440* |

The above body weights indicated with an * are significantly different than controls ($p < 0.05$). All of these body weights are mean values.

A statistically significant increase ($p<0.05$) was noted in the body weight of the 3 ppm (5.0%) and 30 ppm (4.2%) magnesium sulfate trihydrate adduct of 2,2'-dithiobispyridine-1,1'-dioxide treated groups vs. the controls after 8 weeks. The dose of 100 ppm caused a signficant decrease ($p<0.05$) in body weight (7.6%) since the dose was too high causing toxicity (i.e. paresis of wings and legs and ataxia).

What is claimed is:

1. A method for improving the growth response in poultry which comprises;
    orally administering to said poultry a growth-promoting amount of at least one metallic salt of pyridine-2-thione-N-oxide.

2. The method of claim 1 wherein said poultry is turkey.

3. The method of claim 1 wherein said poultry is chicken.

4. The method of claim 1 wherein said metallic salt is zinc pyridine-2-thione-N-oxide.

5. The method of claim 1 wherein said metallic salt is sodium pyridine-2-thione-N-oxide.

6. A method of improving the growth response in poultry which comprises
    feeding said poultry a feed composition comprising a growth-promoting amount of at least one metallic salt of pyridine-2-thione-N-oxide.

7. The method of claim 6 wherein said poultry is turkey.

8. The method of claim 6 wherein said poultry is chicken.

9. The method of claim 6 wherein said metallic salt is zinc pyridine-2-thione-N-oxide.

10. The method of claim 6 wherein said metallic salt is sodium pyridine-2-thione-N-oxide.

11. The method of claim 9 wherein the amount of zinc pyridine-2-thione-N-oxide is from about 3 parts to about 75 parts per million parts by weight of the feed composition.

12. A poultry feed composition comprising a growth-promoting amount of at least one metallic salt of pyridine-2-thione-N-oxide.

13. The feed composition of claim 12 wherein said metallic salt is zinc pyridine-2-thione-N-oxide.

14. The feed composition of claim 12 wherein said metallic salt is sodium pyridine-2-thione-N-oxide.

* * * * *